(12) United States Patent
Nagamoto et al.

(10) Patent No.: US 11,247,073 B2
(45) Date of Patent: Feb. 15, 2022

(54) PARTICLE RADIATION THERAPY APPARATUS

(71) Applicants: KABUSHIKI KAISHA TOSHIBA, Minato-ku (JP); TOSHIBA ENERGY SYSTEMS & SOLUTIONS CORPORATION, Kawasaki (JP)

(72) Inventors: Yoshifumi Nagamoto, Yokohama (JP); Shigeru Kasai, Yokohama (JP); Takeshi Yoshiyuki, Yokohama (JP)

(73) Assignees: KABUSHIKI KAISHA TOSHIBA, Minato-ku (JP); TOSHIBA ENERGY SYSTEMS & SOLUTIONS CORPORATION, Kawasaki (JP)

(*) Notice: Subject to any disclaimer, the term of this patent is extended or adjusted under 35 U.S.C. 154(b) by 40 days.

(21) Appl. No.: 16/929,161

(22) Filed: Jul. 15, 2020

(65) Prior Publication Data

US 2020/0338367 A1    Oct. 29, 2020

Related U.S. Application Data

(63) Continuation of application No. PCT/JP2019/001462, filed on Jan. 18, 2019.

(30) Foreign Application Priority Data

Feb. 9, 2018    (JP) .............................. JP2018-021627

(51) Int. Cl.
*A61N 5/10* (2006.01)
*A61B 6/02* (2006.01)
(Continued)

(52) U.S. Cl.
CPC ............ *A61N 5/1078* (2013.01); *A61B 6/025* (2013.01); *A61B 6/0407* (2013.01);
(Continued)

(58) Field of Classification Search
None
See application file for complete search history.

(56) References Cited

U.S. PATENT DOCUMENTS 4,501,011 A * 2/1985 Hauck .................. A61B 6/4464
378/190
2006/0163495 A1    7/2006 Hiramoto et al.
(Continued)

FOREIGN PATENT DOCUMENTS

CN    107569783 A    1/2018
EP    2 353 648 A1    8/2011
(Continued)

OTHER PUBLICATIONS

International Search Report dated Mar. 12, 2019 in PCT/JP2019/001462 filed on Jan. 18, 2019, citing documents AA & AO-AQ therein, 1 page.

*Primary Examiner* — Hoon K Song
(74) *Attorney, Agent, or Firm* — Oblon, McClelland, Maier & Neustadt, L.L.P.

(57) ABSTRACT

A particle radiation therapy apparatus 10 includes: a bed 15 for positioning of a patient 12; irradiation ports 16 (16*a*, 16*b*) that output a particle beam in a treatment room 11; a horizontal-direction imaging unit 21 composed of a first X-ray source 25 and a first X-ray detector 26 that face each other with the bed 15 interposed therebetween; a vertical-direction imaging unit 22 composed of a second X-ray source 27 and a second X-ray detector 28 that face each other with the bed 15 interposed therebetween; a storage room 18 for housing the first X-ray detector 26 under the floor when the horizontal-direction imaging unit 21 is not used; and a support member 23 that moves the first X-ray detector 26 above the floor and supports it between the bed
(Continued)

15 and the side of the irradiation ports 16 when the horizontal-direction imaging unit 21 is used.

9 Claims, 5 Drawing Sheets

(51) Int. Cl.
 *A61B 6/04* (2006.01)
 *A61B 6/00* (2006.01)
(52) U.S. Cl.
 CPC .......... *A61B 6/4429* (2013.01); *A61N 5/1043* (2013.01); *A61N 2005/1087* (2013.01)

(56) References Cited

U.S. PATENT DOCUMENTS

| | | | |
|---|---|---|---|
| 2007/0081632 | A1 | 4/2007 | Fadler |
| 2011/0182411 | A1 | 7/2011 | Shinagawa et al. |
| 2018/0028835 | A1 | 2/2018 | Bennett et al. |
| 2018/0289981 | A1 | 10/2018 | Nagamoto et al. |
| 2019/0240510 | A1* | 8/2019 | Dargis .................. A61B 6/542 |
| 2020/0009404 | A1* | 1/2020 | Fujii .................... A61N 5/1037 |

FOREIGN PATENT DOCUMENTS

| | | |
|---|---|---|
| JP | 01-113700 A | 5/1989 |
| JP | 4130680 B2 | 8/2008 |
| JP | 2011-072460 A | 4/2011 |
| JP | 2011-152346 A | 8/2011 |
| JP | 2016-129639 A | 7/2016 |
| JP | 2017-064018 A | 4/2017 |
| JP | 2017-064018 A5 | 4/2017 |
| WO | WO 2013/080111 A1 | 6/2013 |

* cited by examiner

PARTICLE RADIATION THERAPY APPARATUS

CROSS-REFERENCE TO RELATED APPLICATIONS

This application is a Continuation Application of No. PCT/JP2019/001462, filed on Jan. 18, 2019, and the PCT application is based upon and claims the benefit of priority from Japanese Patent Application No. 2018-021627, filed on Feb. 9, 2018, the entire contents of which are incorporated herein by reference.

TECHNICAL FIELD

Embodiments of the present invention relate to a particle radiation therapy apparatus of a fixed irradiation type.

BACKGROUND

In the widely known particle radiation therapy technique, a particle beam composed of, for example, carbon ions and cations is applied to a lesion tissue (cancer) of a patient to perform treatment. The particle beam loses its kinetic energy so as to speed down as it passes through the patient's body while undergoing resistance that is almost inversely proportional to the square of the velocity, and suddenly stops when the velocity of the particle beam drops to a certain velocity. Near the stopping point of the particle beam, high energy called Bragg peak is emitted.

In the particle radiation therapy technique, the Bragg peak is aligned with the lesion of the patient and the treatment is performed while damage to normal tissues is being reduced. According to the particle radiation therapy technique, the lesion tissue can be pinpointly killed without damaging the normal tissues, and thus, burden on the patient is less than that of surgery and medication. Consequently, early return to society after the treatment can be expected.

In order to reliably kill the lesion cells and avoid damage to normal cells, in some cases, the particle beam is radiated onto the lesion for a plurality of times from respective different incident directions. The particle radiation therapy apparatus is roughly classified into a rotating gantry type and a fixed irradiation type depending on the installation specifications of its irradiation port for making the particle beam incident on the lesion.

In the rotating gantry type, the irradiation port and the beam transport path are installed in the rotating gantry such that the particle beam can be radiated toward the rotating axis of the rotating gantry. The bed on which the patient is lying is moved and the position is checked so that the lesion is positioned at the aim (i.e., isocenter) of the particle beam being set on the rotation axis of the rotating gantry. Further, the incident direction of the particle beam is changed by rotating the rotating gantry without changing the posture of the patient and/or the position of the bed.

In the fixed irradiation type, the particle beam passes through the beam transportation path fixed in the facility and is radiated through the irradiation port installed in the treatment room. Although the bed with the patient lying thereon is moved and the position is checked so that the lesion is positioned at the aim (i.e., isocenter) of the particle beam similarly to the rotating gantry type, the posture of the patient and/or the position of the bed are changed in some cases in order to change the incident direction of the particle beam.

A particle radiation therapy facility is a large-scale facility including an accelerator that generates particle beams. Thus, a particle radiation therapy facility is often configured with multiple treatment rooms for one accelerator that generates particle beams in order to reduce treatment costs and improve treatment throughput. Each of the plurality of treatment rooms can be provided with an irradiation port with different specifications such as the rotating gantry type and the fixed irradiation type. Thus, an optimal treatment room is selected depending on the purpose. Generally, the fixed irradiation type can reduce the initial investment cost.

In the particle radiation therapy apparatus of the fixed radiation type, one or more irradiation ports are often installed in each treatment room such that the particle beam is fixedly radiated in at least one of the horizontal direction, the vertical direction, and the oblique 45° direction. Further, in order to check that the lesion is accurately positioned on the trajectory of the particle beam, the particle radiation therapy apparatus is provided with two sets of X-ray imaging devices, imaging directions of which are orthogonal to each other.

SUMMARY

Problems to be Solved by Invention

Since the maintenance cost of equipment for particle radiation therapy is high, in order to efficiently treat many patients, particle radiation therapy is required to shorten the occupation time of the treatment room per one treatment. In order to reduce this occupation time, in the treatment room, before and after the positioning of the bed, a plurality of preparatory works are performed in parallel by medical workers in charge of them. Thus, in the treatment room crowded with many medical workers, it is required to ensure work safety.

Accordingly, it is necessary for the treatment room to have sufficient effective space around the isocenter for moving the bed and working of medical staff. Hence, it is desirable that the X-ray sources and the X-ray detectors of the X-ray imaging devices are in an evacuated state from the periphery of the bed and the irradiation port except when needed.

However, from the viewpoint of effective use of the space, it is not appropriate to provide an extra dedicated space for evacuating the devices to positions where the evacuated devices do not hinder the movement of the bed and the work of the medical staff.

In view of the above-described circumstances, an object of embodiments of the present invention is to provide a particle radiation therapy apparatus that can evacuate an X-ray imaging apparatus and improve workability of medical staff without wastefully occupying the effective space of the treatment room.

PRIOR ART DOCUMENT

Patent Document

[Patent Document 1] JP 2017-164204 A

DETAILED DESCRIPTION

First Embodiment

Hereinbelow, embodiments of the present invention will be described by referring to the accompanying drawings.

Figure 1:
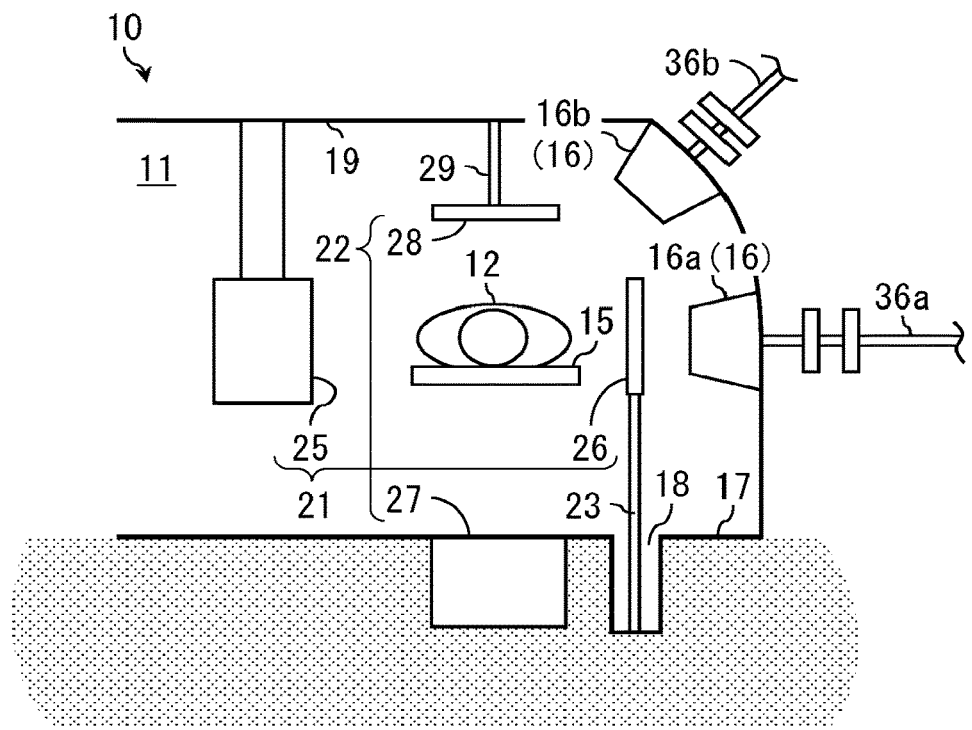
FIG. 1 is a diagram illustrating a treatment room in which a particle radiation therapy apparatus according to the first embodiment of the present invention is installed.

FIG. 1 illustrates a treatment room 11 in which the particle radiation therapy apparatus 10 according to the first embodiment is installed. The particle radiation therapy apparatus 10 includes: a bed 15 that moves in the space of the treatment room 11 so as to perform positioning of a patient 12; irradiation ports 16 (16a, 16b) configured to output a particle beam, which has been transported through fixed beam transport paths 36 (36a, 36b), in the treatment room 11; a horizontal-direction imaging unit 21 composed of a first X-ray source 25 and a first X-ray detector 26 that face each other along the horizontal line with the bed 15 interposed therebetween; a vertical-direction imaging unit 22 composed of a second X-ray source 27 and a second X-ray detector 28 that face each other along the vertical line with the bed 15 interposed therebetween; a storage room 18 provided on a floor side 17 of the treatment room 11 for housing the first X-ray detector 26 under the floor when the horizontal-direction imaging unit 21 is not in use; and a support member 23 housed in the storage room 18 together with the first X-ray detector 26 when the horizontal-direction imaging unit 21 is not used. When the horizontal-direction imaging unit 21 is used, this support member 23 moves the first X-ray detector 26 above the floor and supports it between the bed 15 and the side of the irradiation ports 16.

Figure 2:
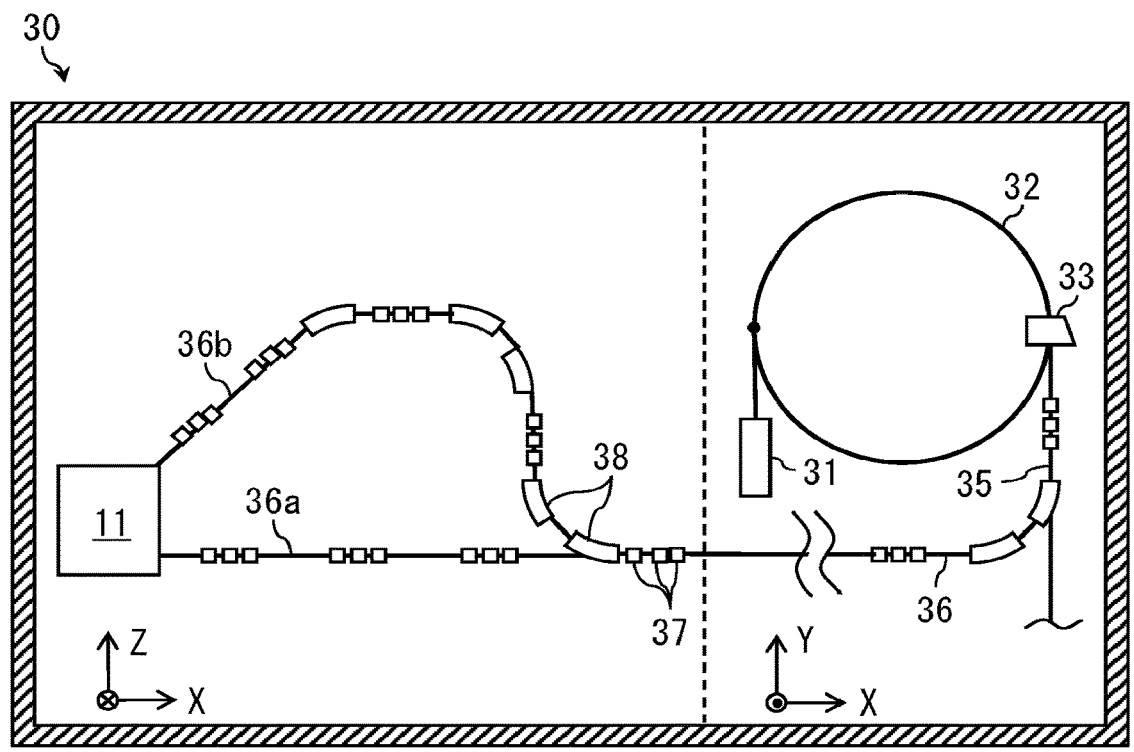
FIG. 2 is a schematic view of a facility in which the particle radiation therapy apparatus according to each embodiment is installed.

FIG. 2 is a schematic diagram of the facility 30 in which the particle radiation therapy apparatus 10 according to each embodiment is installed. Although the vertical plane (X-Z) including the longitudinal cross-section of the treatment room 11 is in twisted positional relationship with the horizontal plane (X-Y) including the circular accelerator 32, the horizontal plane (X-Y) and the vertical plane (X-Z) are shown in the same sheet in FIG. 2. In the facility 30, only one treatment room 11 of the fixed irradiation type is described among a plurality of treatment rooms, and description of the other treatment rooms is omitted.

In generation of the particle beam, ions (heavy particles or proton ions) generated by an ion source (not shown) are accelerated by a linear accelerator 31, then the accelerated ions are made incident on the circular accelerator 32 so as to increase the energy up to the setting energy, and thereby the particle beam is generated.

The circular accelerator 32 is a synchrotron or the like. The circular accelerator 32 outputs the particle beam, which is generated by accelerating charged particles such as $C^{6+}$ generated by the ion source (not shown) to about 70% to 80% of the speed of light, from an exit deflector 33 to the beam transport path (i.e., main line) 35.

The particle beam is transported to the treatment room 11 by the plurality of beam transport paths 36 (branching lines; only one of the beam transport paths 36 is shown in the drawings) branched from the beam transport path (i.e., main line) 35. Moreover, the illustrated one of the beam transport paths 36 is further branched into two, and the beam transport path 36a is connected to the irradiation port 16a (FIG. 1) configured to output the particle beam, irradiation direction of which is fixed in the horizontal direction. The other (36b) of the branched beam transport paths is connected to the irradiation port 16b (FIG. 1) configured to output the particle beam, irradiation direction of which is fixed at 45°.

In the beam transport path 35 and the beam transport paths 36 (36a, 36b) for transporting the particle beam, a quadrupole electromagnet 37 configured to control convergence and divergence of the beam, a bending electromagnet 38 configured to bend the beam trajectory, and a steering electromagnet configured to correct the deviation of the beam trajectory are sequentially disposed.

Returning to FIG. 1, the beam transport paths 36 (36a, 36b) are connected to the treatment room 11 from outside, and the irradiation ports 16 (16a, 16b) are formed on the side of its inner space. In the figure, the plurality of irradiation ports 16 (16a, 16b) are provided so as to correspond to each of the plurality of beam transport paths 36 (36a, 36b). The irradiation ports 16 are not limited to the illustrated form. In some cases, one irradiation port 16 is configured to move on the wall surface of the treatment room 11 and output the particle beam from the plurality of beam transport paths 36 (36a, 36b).

Although the illustrated irradiation ports 16 (16a, 16b) exemplify those in which the irradiation direction of the particle beam is fixed at 0° and 45° with respect to the horizontal line, the irradiation direction is not limited to this aspect. Irradiation ports 16 in which the irradiation direction of the particle beam is fixed at an arbitrary angle within the range of 0° to 90° can be used.

Although the illustrated beam transport paths 36 (36a, 36b) are configured as two systems, the beam transport paths 36 (36a, 36b) may be configured as one system or may be configured as three or more systems.

As the irradiation method from the irradiation ports 16, there are an expanded beam method (i.e., wobbler irradiation method) and a three-dimensional scanning method.

The expanded beam method is a method in which the diameter of the particle beam is expanded to the lesion size or more and the irradiation area is limited by a collimator so as to match the lesion shape.

The three-dimensional scanning method is a method in which a narrowly focused beam is made to scan the lesion area at high speed by a scanning electromagnet so as to fill the lesion area.

When the expanded beam method is adopted, inside the irradiation ports 16 and in the beam transport paths 36 (36a, 36b) being in the vicinity thereof, a wobbler electromagnet (not shown) configured to expand the beam diameter, a collimator configured to set the shape of the beam cross-section, a range shifter (not shown) configured to set penetration depth, and the like are provided. Strictly speaking, the expanded beam method cannot match the irradiation region with the lesion shape three-dimensionally, so it has been pointed out that there is a limit to reducing the effect on normal cells around the lesion.

When the three-dimensional scanning method is adopted, inside the irradiation ports 16 and in the beam transport paths 36 (36a, 36b) being in the vicinity thereof, two sets of scanning electromagnets (not shown), a range shifter (not shown) for setting the penetration depth, and the like are disposed. The two sets of scanning electromagnets deflect and scan the particle beam in two directions, which are orthogonal to each other and are orthogonal to the beam traveling direction.

In the three-dimensional scanning method, the collimator, which is indispensable in the expanded beam method, is not necessary, so the irradiation ports 16 can be miniaturized. Since the number of required devices is small, the distance between the patient and the end of the vacuum duct can be shortened, whereby the transport distance of the particle beam in the air can be shortened and scattering can be suppressed.

In the following, a description will be given for the case where the three-dimensional scanning method is adopted.

The X-ray imaging apparatus is configured of both the horizontal-direction imaging unit 21 and the vertical-direction imaging unit 22. The X-ray detector 26 (i.e., first X-ray detector 26) of the horizontal-direction imaging unit 21 is disposed so as to be located between the irradiation port 16a and the bed 15 when being used. This first X-ray detector 26 is supported by the support member 23 from the floor side 17 of the treatment room 11. As described below, when the horizontal-direction imaging unit 21 is not used, the first X-ray detector 26 is housed in the storage room 18 provided on the floor side 17 together with the support member 23.

The X-ray source 25 (i.e., first X-ray source 25) of the horizontal-direction imaging unit 21 is disposed at the position where the X-ray source 25 faces the first X-ray detector 26 along the horizontal line with the bed 15 interposed therebetween. The first X-ray source 25 is supported from the ceiling surface 19 of the treatment room 11 via a suspension device. When the horizontal-direction imaging unit 21 is not used, the first X-ray source 25 is driven vertically upward by the suspension device so as to approach the ceiling surface 19.

The above-described arrangement configuration of the horizontal-direction imaging unit 21 contributes to the improvement of utilization efficiency of the internal space of the treatment room 11. When the horizontal-direction imaging unit 21 is not used, the horizontal-direction imaging unit 21 does not prevent access to the isocenter or the vicinity of the bed 15. Since the first X-ray detector 26 having a smaller thickness than the first X-ray source 25 is disposed between the irradiation port 16a and the bed 15 and the first X-ray source 25 is disposed on the opposite side, the distance between the patient 12 and the irradiation port 16a can be shortened. This configuration maximizes the advantage of the three-dimensional scanning method, i.e., the advantage that scattering of the particle beam is suppressed by shortening the transportation distance of the particle beam in the air.

The X-ray source 27 (i.e., second X-ray source 27) of the vertical-direction imaging unit 22 is installed on the floor side 17 of the treatment room 11. The X-ray detector 28 (i.e., second X-ray detector 28) of the vertical-direction imaging unit 22 is disposed at the position where the X-ray detector 28 faces the second X-ray source 27 with the bed 15 interposed therebetween along the vertical line. The second X-ray detector 28 is fixed to the ceiling surface 19 of the treatment room 11 via a support member 29.

Since the X-ray imaging apparatus is composed of the horizontal-direction imaging unit 21 and the vertical-direction imaging unit 22, generally, two-directional fluoroscopic images of the patient 12, who lies on the bed 15 with the front of the body facing the ceiling surface 19 of treatment room 11, are obtained as a sagittal image and a coronal image. This artificially facilitates determination of adequacy of positioning of the bed 15 in the coordinate space of the treatment room 11.

The first X-ray detector 26 and the second X-ray detector 28 are, for example, flat panel detectors (FPDs) and/or image intensifiers. The first X-ray detector 26 and the second X-ray detector 28 are not limited to FPDs and image intensifiers. Each of the first X-ray detector 26 and the second X-ray detector 28 may be any appropriate configuration that detects the energy of X-rays outputted from the X-ray sources 25 and 27 and transmitted through the patient 12 and converts the energy into pixel brightness information so as to form a fluoroscopic image of the patient 12.

The particle radiation therapy is a treatment technique for irradiating the lesion of the patient with the particle beam and destroying it. Accordingly, in the particle radiation therapy, unless the particle beam is accurately applied to the location of the lesion, even normal tissue may be destroyed.

Thus, in the particle radiation therapy, prior to irradiating the patient 12 with the particle beam, CT imaging is performed at a location different from this treatment room 11 for obtaining voxel data of the inside of the patient's body such that the lesion position is three-dimensionally specified. On the basis of on the voxel data of the inside of the patient's body, a treatment plan for determining the irradiation direction and irradiation intensity of the particle beam is executed such that the irradiation to the normal tissue is reduced.

In this treatment plan, X-ray CT (Computed Tomography) or the like is used to generate a stereoscopic image (voxel data) inside the body including the lesion with the same posture of the patient 12 fixed to the bed 15 in the treatment room 11 for receiving the particle beam irradiation. On the basis of the lesion area specified by the voxel data, conditions of the particle beam such as an irradiation position, an irradiation angle, irradiation range, dose, and number of irradiation times are determined.

Further, a reconstructed image (DRR: Digitally Reconstructed Radiograph) is generated by projecting the voxel data on a virtual plane corresponding to the positions and angles of the X-ray detectors 26 and 28 from the virtual viewpoint corresponding to the positions of the X-ray sources 25 and 27.

The position of the virtual viewpoint and the position and angle of the virtual plane required to generate this reconstructed image (DRR) are based on the design information of the X-ray sources 25 and 27 and the X-ray detectors 26 and 28. The design information includes the mechanical position and angle in the spatial coordinate system of the treatment room 11 for the X-ray sources 25 and 27 and the X-ray detectors 26 and 28 that constitute the horizontal-direction imaging unit 21 and the vertical-direction imaging unit 22.

The positional information of the bed 15 for lying the patient 12 in the spatial coordinate system of the treatment room 11 is determined in such a manner that the position of the lesion having been set on the voxel data matches the aim of the particle beam having been set in the spatial coordinate system of the treatment room 11.

At a later date, the patient 12 carried to the treatment room 11 is fixed to the bed 15, the bed 15 is moved to the spatial coordinates of the treatment room 11 on the basis of the positional information determined in the treatment plan, and the lesion of the patient is aligned with the aim of the particle beam. Further, the patient 12 is imaged by using the horizontal-direction imaging unit 21 and the vertical-direction imaging unit 22 to obtain X-ray fluoroscopic images.

When the horizontal-direction and vertical-direction X-ray fluoroscopic images of the patient 12 imaged in the spatial coordinate system of the treatment room 11 match the DRR images virtually reconstructed from the voxel data at the stage of the treatment plan, it can be confirmed that the position of the lesion of the patient 12 matches the aim of the particle beam. Although many automated methods have been proposed for this confirmation, in the end, it will be verified and confirmed visually by a human. When the X-ray fluoroscopic images do not match the DRR images, the bed 15 is moved to adjust its position.

In the particle radiation therapy, in some cases, radiation of the particle beam onto the patient 12 is performed several times to several tens of times over a plurality of days while changing the irradiation ports 16 (16a, 16b) and/or changing the posture of the patient on the bed 15. Thus, imaging of the patient 12 with the horizontal-direction imaging unit 21 and the vertical-direction imaging unit 22 and work of checking coincidence between the position of the lesion and the aim of the beam are performed each time the patient is irradiated with the particle beam.

Figure 3A:
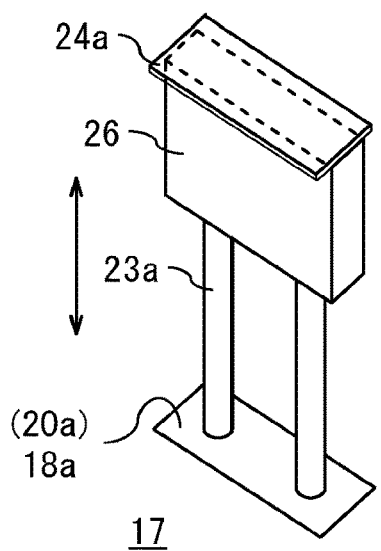
FIG. 3A is a perspective view of an X-ray detector of a horizontal-direction imaging unit to be applied to the particle radiation therapy apparatus according to the first embodiment.
Figures 3B, 3C:
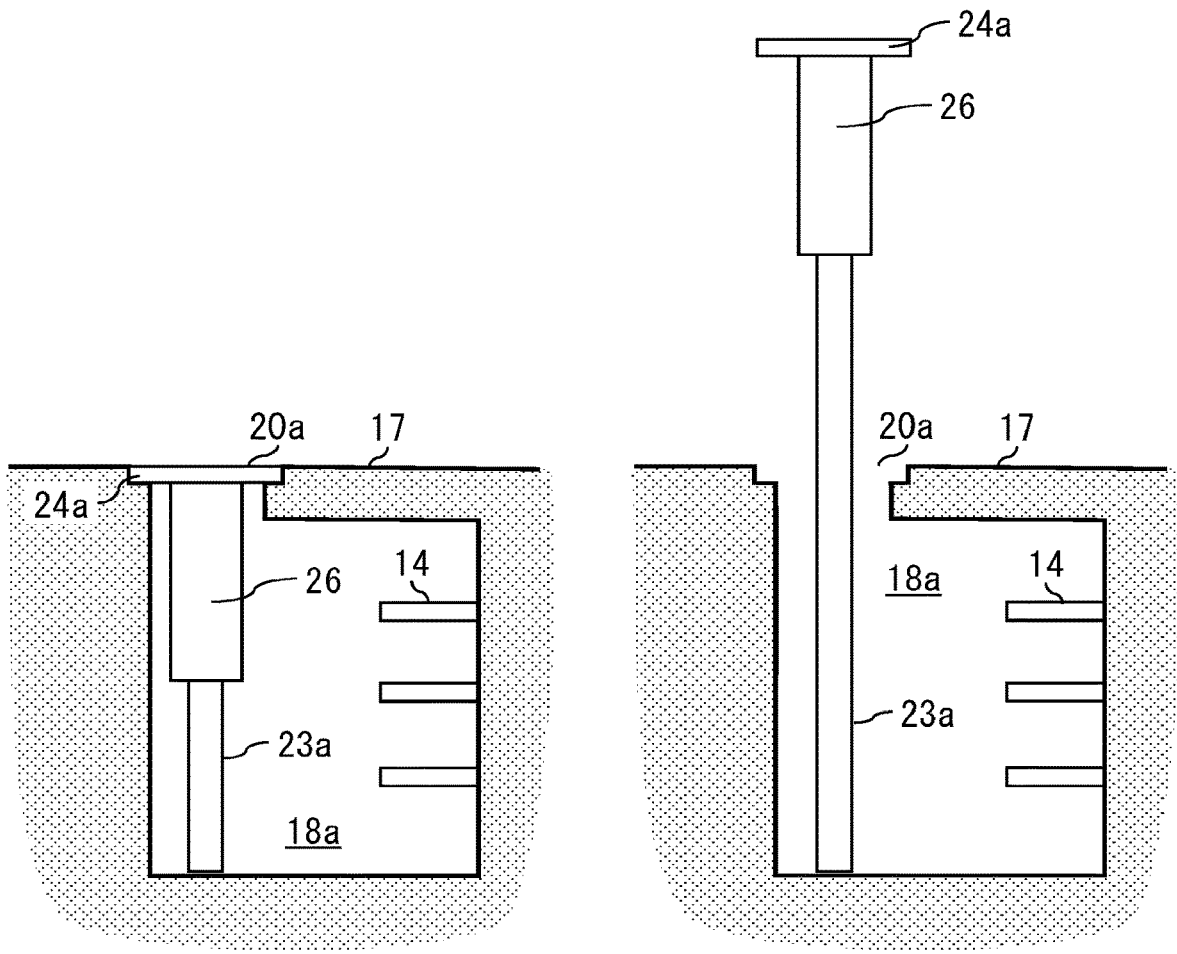
FIG. 3B is a longitudinal cross-sectional view showing a state where the X-ray detector according to the first embodiment is housed in the storage room.
FIG. 3C is a longitudinal cross-sectional view showing a state where the X-ray detector according to the first embodiment is in use.

FIG. 3A is a perspective view of the X-ray detector of the horizontal-direction imaging unit to be applied to the particle radiation therapy apparatus according to the first embodiment. FIG. 3B is a longitudinal cross-sectional view showing a state where the X-ray detector is housed in the storage room. FIG. 3C is a longitudinal cross-sectional view showing a state where the X-ray detector is in use.

In the particle radiation therapy apparatus according to the first embodiment, the storage room 18a provided on the floor side 17 is provided with a first support member 23a that supports the X-ray detector 26 and linearly displaces it in the vertical direction. The first support member 23a is composed of, for example, a hydraulic cylinder, and performs a predetermined stroke operation of about 1.5 m until the rod extends due to hydraulic pressure supply and stops at the stopper. When the hydraulic pressure is released, the rod returns by its built-in spring.

A cover member 24a provided on the upper end of the X-ray detector 26 closes an opening 20a of the storage room 18a flatly with respect to the floor surface 17 under the state where the X-ray detector 26 is stored in the storage room 18a. At least the upper face of the cover member 24a is made of the same material as the floor surface 17. Further, the storage room 18a is provided with a maintenance space for inspecting and repairing the X-ray detectors and the supporting members. In the maintenance space, an entrance path different from the opening 20a is provided, and a storage shelf 14 for maintenance parts jigs and tools is provided.

As shown in FIG. 3B, the X-ray detector 26 is stored in the storage room 18a except when X-ray fluoroscopic imaging is performed. As shown in FIG. 3A and FIG. 3C, when X-ray fluoroscopic imaging is performed, the first support member 23a is raised. As to the operation of the first support member 23a, an rising operation in response to an imaging preparation signal or imaging permission signal of the X-ray source and a storage operation in response to an imaging interruption signal or imaging completion signal of the X-ray source are performed by a control device that transmits the imaging preparation signal, the imaging permission signal, the imaging interruption signal, and the imaging completion signal.

This makes it easier for medical staff to access the vicinity of the bed 15 at the time of positioning of the patient 12 and reduces the risk of stumbling. Additionally, the material of the top face of the cover and the floor material are the same, and thus, feeling of unity is created and pressure and discomfort can be reduced. Moreover, the storage room 18 of the X-ray detector 26 is configured on the floor side 17 of the treatment room 11, and consequently, it is not necessary to provide extra space for evacuating the X-ray detector 26. Hence, it can be configured with the minimum facility area. Furthermore, in the first embodiment, the opening 20a of the storage chamber can be made small.

Second Embodiment

Figure 4A:
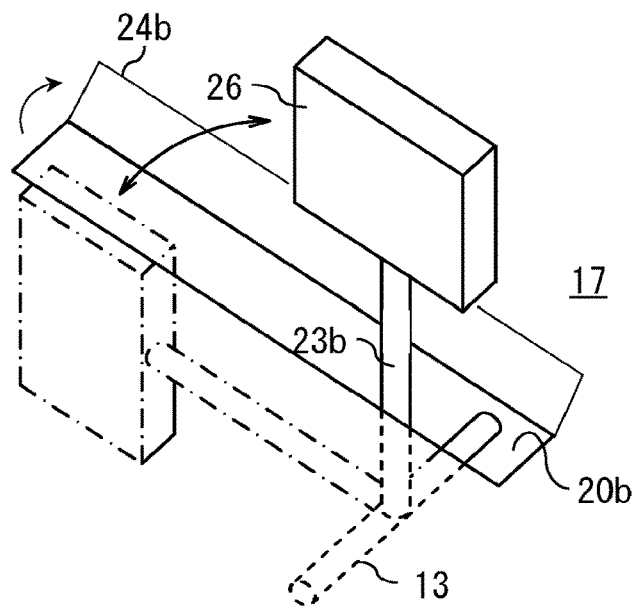
FIG. 4A is a perspective view of the X-ray detector of the horizontal-direction imaging unit to be applied to the particle radiation therapy apparatus according to the second embodiment.
Figure 4B:
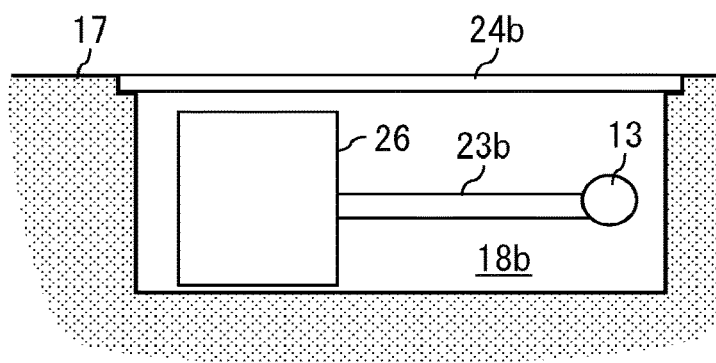
FIG. 4B is a longitudinal cross-sectional view showing a state where the X-ray detector according to the second embodiment is housed in the storage room.
Figure 4C:
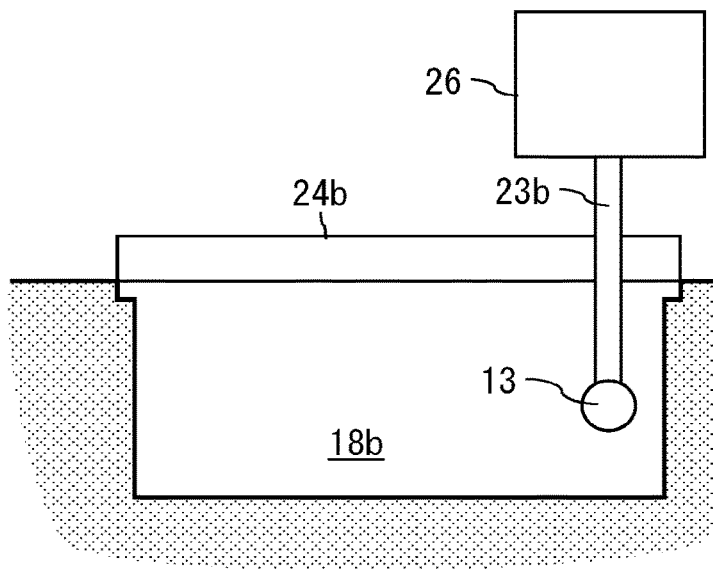
FIG. 4C is a longitudinal cross-sectional view showing a state where the X-ray detector according to the second embodiment is in use.

Next, the second embodiment of the present invention will be descried by referring to FIG. 4A to FIG. 4C. In the second embodiment, the entire configuration of the horizontal imaging unit excluding the X-ray detector is the same as that of the first embodiment, and duplicated description is omitted.

FIG. 4A is a perspective view of the X-ray detector of the horizontal-direction imaging unit to be applied to the particle radiation therapy apparatus according to the second embodiment. FIG. 4B is a longitudinal cross-sectional view showing a state where the X-ray detector is housed in the storage room. FIG. 4C is a longitudinal cross-sectional view showing a state where the X-ray detector is in use.

In the particle radiation therapy apparatus according to the second embodiment, the storage room 18b provided on the floor side 17 is provided with a second support member 23b that supports the X-ray detector 26 and rotationally displaces the X-ray detector 26 in the direction along the detection surface. The rotating member 13 is connected to the base end of the second support member 23b. For example, the second support member 23b is made of a metal pipe, the rotating member 13 is made of a metal shaft, a speed reducer, an electric motor, and an encoder. The electric motor is controlled on the basis of the encoder to rotate it to a predetermined position.

A cover member 24b provided on an opening 20b of the storage room 18b closes the opening 20b of the storage room 18b flatly with respect to the floor surface 17 under the state where the X-ray detector 26 is stored in the storage room 18b. In conjunction with the rotational displacement of the second support member 23b, the cover member 24b performs an opening operation so as not to interfere with each.

As shown in FIG. 4B, the X-ray detector 26 is housed in the storage room 18b except when X-ray fluoroscopic imaging is performed. As shown in FIG. 4A and FIG. 4C, when X-ray fluoroscopic imaging is performed, the rotating member 13 connected to the base end of the second support member 23b rotates such that the X-ray detector 26 is set to the imaging position. In the second embodiment, the vertical depth of the storage room 18b can be reduced.

Third Embodiment

Next, the third embodiment of the present invention will be described by referring to FIG. 5A to FIG. 5C. In the third embodiment, the entire configuration of the horizontal imaging unit excluding the X-ray detector is the same as that of the first embodiment, and duplicated description is omitted.

Figure 5A:
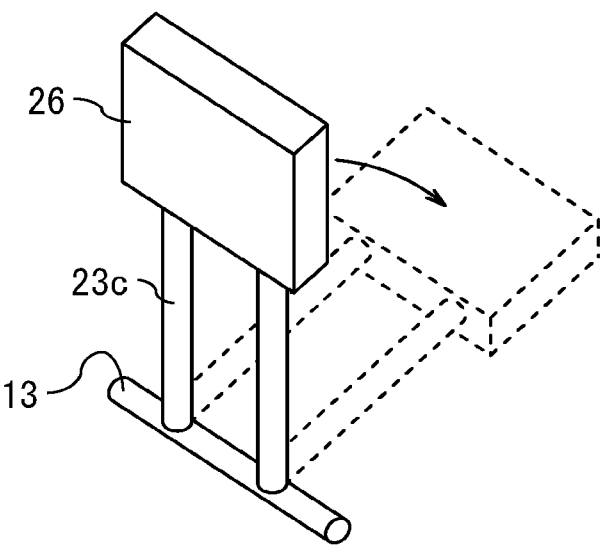
FIG. 5A is a perspective view of the X-ray detector of the horizontal-direction imaging unit to be applied to the particle radiation therapy apparatus according to the third embodiment.

FIG. 5A is a perspective view of the X-ray detector of the horizontal-direction imaging unit to be applied to the particle radiation therapy apparatus according to the third embodiment. FIG. 5B is a longitudinal cross-sectional view showing a state where the X-ray detector is housed in the storage room. FIG. 5C is a longitudinal cross-sectional view showing a state where the X-ray detector is in use.

In the particle radiation therapy apparatus according to the third embodiment, the storage room 18c provided on the floor side 17 is provided with a third support member 23c that supports the X-ray detector 26 and rotationally displaces the X-ray detector 26 in the direction perpendicular to its detection surface. The rotating member 13 is connected to the base end of the third support member 23c. For example, the third support member 23c is configured of an FRP, and the rotating member 13 is configured of a shaft and a spring. When a latch (not shown) provided in the storage room 18c is released by stepping the pedal (not shown) provided on the floor side 17, the rotating member 13 is rotated by spring force to a predetermined position, hits a stopper provided, and stops at that position. When storing the X-ray detector 26, the staff pushes it back and latches it again.

The particle radiation therapy apparatus according to the third embodiment is provided with a cover member 24c for closing an opening 20c of the storage room 18c provided on the floor side 17 flatly with respect to the surface on the floor side 17 under the state where the first X-ray detector 26 is stored in the storage room 18c.

Figure 5B:
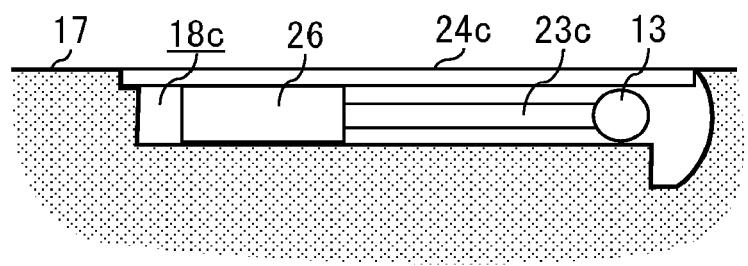
FIG. 5B is a longitudinal cross-sectional view showing a state where the X-ray detector according to the third embodiment is housed in the storage room.
Figure 5C:
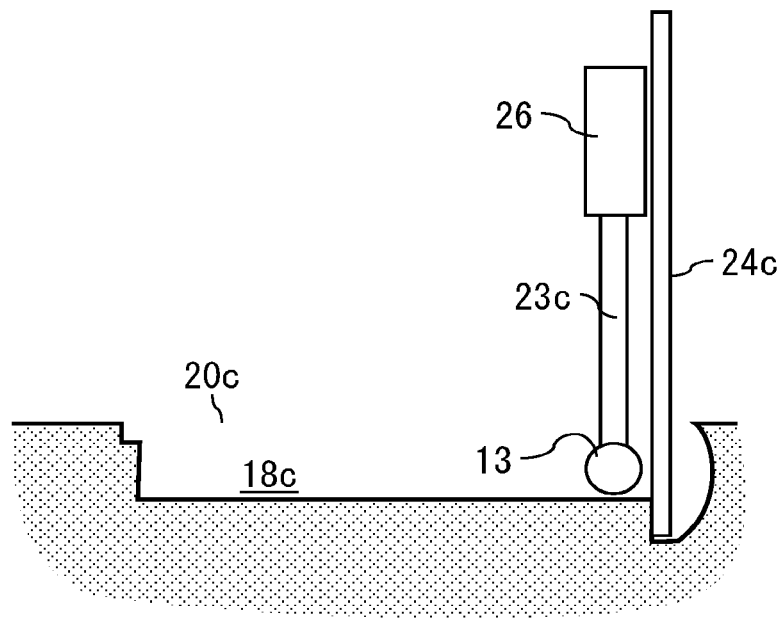
FIG. 5C is a longitudinal cross-sectional view showing a state where the X-ray detector according to the third embodiment is in use.

As shown in FIG. 5B, the X-ray detector 26 is stored in the storage room 18c except when X-ray fluoroscopic imaging is performed. As shown in FIG. 5A and FIG. 5C, when X-ray fluoroscopic imaging is performed, the member 13 connected to the base end of the third support member 23c is rotated such that the X-ray detector 26 is set to the imaging position. In the third embodiment, the vertical depth of the storage room 18c can be further reduced. Further, the contact surface area of the stopper can be secured most readily, and thus, highly accurate positioning of the X-ray detector 26 can be guaranteed.

Fourth Embodiment

Figure 6:
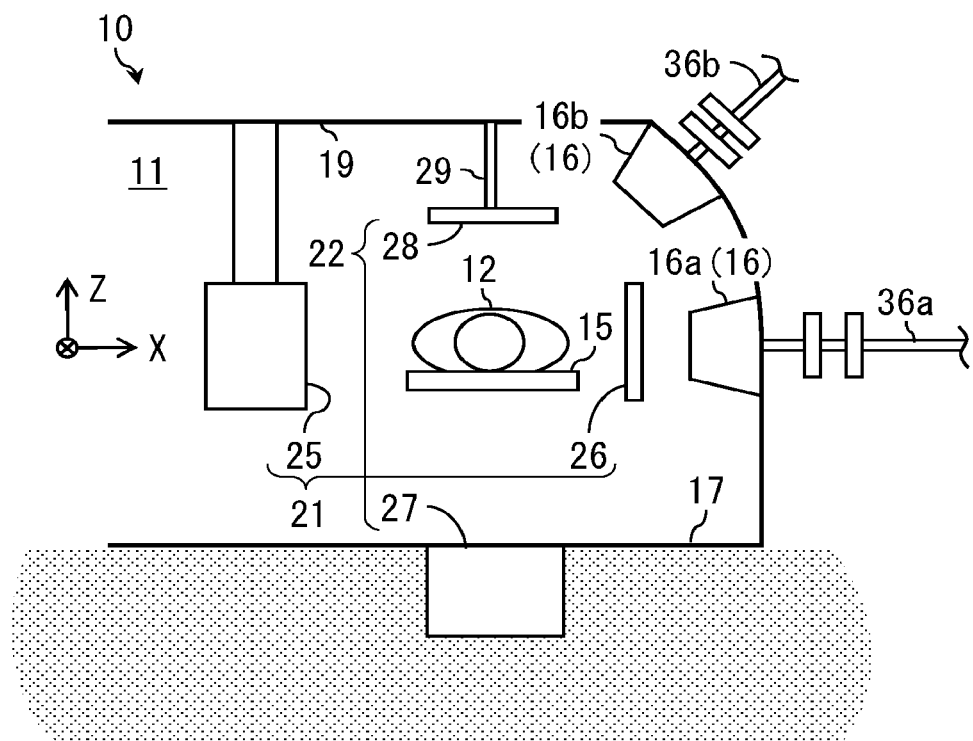
FIG. 6 is a diagram illustrating a treatment room in which the particle radiation therapy apparatus according to the fourth embodiment of the present invention is installed.

Next, the fourth embodiment of the present invention will be described by referring to FIG. 6 and FIG. 7. FIG. 6 is a diagram showing the particle radiation therapy apparatus according to the fourth embodiment of the present invention. In FIG. 6, components having the same configuration or function as those in FIG. 1 are denoted by the same reference signs, and duplicate description is omitted.

The particle radiation therapy apparatus according to the fourth embodiment is provided with a fourth support member 23d (FIG. 7) that is installed in the treatment room 11 at a position other than the floor side 17. When the horizontal-direction imaging unit 21 is not in use, the fourth support member 23d displaces the first X-ray detector 26 horizontally and then displaces the first X-ray detector 26 upward. When the horizontal-direction imaging unit 21 is in use, the fourth support member 23d positions the first X-ray detector 26 between the bed 15 and the side of the irradiation ports 16.

Figure 7:
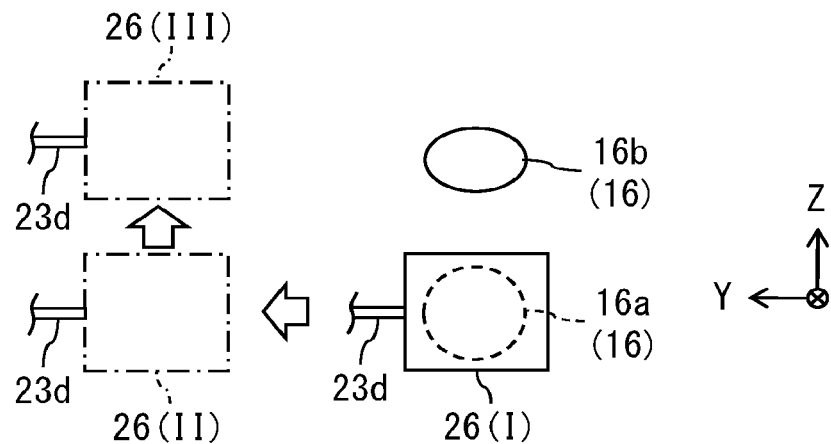
FIG. 7 is a diagram illustrating positions of the X-ray detector of the horizontal-direction imaging unit to be applied to the particle radiation therapy apparatus according to the fourth embodiment when the X-ray detector is in use and when the X-ray detector is housed.

FIG. 7 is a diagram illustrating positions of the X-ray detector of the horizontal-direction imaging unit to be applied to the particle radiation therapy apparatus according to the fourth embodiment when the X-ray detector is in use and when the X-ray detector is housed.

The first X-ray detector 26(I) at the position for performing X-ray imaging is disposed at the position where the first X-ray detector 26(I) faces the irradiation port 16a. After X-ray imaging, the horizontally moved first X-ray detector 26(II) further moves upward so as to avoid the irradiation port 16b and so as not to interfere with working of the medical staff who accesses, and thereby, evacuation of the first X-ray detector 26(III) is completed.

According to the particle radiation therapy apparatus of at least one embodiment described above, the X-ray detector is evacuated to the storage room with a minimum installation area when X-ray imaging is not performed, and thus, the effective space of the treatment room is prevented from being unnecessarily occupied and workability of the medical staff can be improved.

While certain embodiments have been described, these embodiments have been presented by way of example only, and are not intended to limit the scope of the inventions. These embodiments may be embodied in a variety of other forms, and various omissions, substitutions, and changes may be made without departing from the spirit of the inventions. These embodiments and their modifications are included in the accompanying claims and their equivalents as well as included in the scope and gist of the inventions.

The invention claimed is:

1. A particle radiation therapy apparatus comprising:
a bed configured to perform positioning of a patient by moving in space of a treatment room;
an irradiation port configured to output a particle beam in the treatment room, the particle beam having been transported through a fixed beam transportation path;
a horizontal-direction imaging unit provided with a first X-ray source and a first X-ray detector that face each other along a horizontal line with the bed interposed between the first X-ray source and the first X-ray detector;
a vertical-direction imaging unit provided with a second X-ray source and a second X-ray detector that face each other along a vertical line with the bed interposed between the second X-ray source and the second X-ray detector;
a storage room provided on a floor side of the treatment room and configured to store the first X-ray detector under a floor when the horizontal-direction imaging unit is not in use; and a support member configured to be housed in the storage room together with the first X-ray detector when the horizontal-direction imaging unit is not in use, and further configured to move the first X-ray detector above the floor and support the first X-ray detector between the bed and a side of the irradiation ports when the horizontal-direction imaging unit is in use.

2. The particle radiation therapy apparatus according to claim 1, further comprising a scanning electromagnet for performing scanning irradiation of the particle beam.

3. The particle radiation therapy apparatus according to claim 1, wherein an irradiation direction of the particle beam to be outputted from the irradiation port is fixed at 0° with respect to the horizontal line.

4. The particle radiation therapy apparatus according to claim 1, wherein an irradiation direction of the particle beam to be outputted from the irradiation port is fixed within a range of more than 0° and 90° or less with respect to the horizontal line.

5. The particle radiation therapy apparatus according to claim 1, wherein the support member is a first support member that linearly displaces the X-ray detector in a vertical direction.

6. The particle radiation therapy apparatus according to claim 1, wherein the support member is a second support member that rotationally displaces the X-ray detector in a direction along a detection surface of the X-ray detector.

7. The particle radiation therapy apparatus according to claim 1, wherein the support member is a third support member that rotationally displaces the X-ray detector in a direction perpendicular to a detection surface of the X-ray detector.

8. The particle radiation therapy apparatus according to claim 1, further comprising a cover member configured to close an opening of the storage room flatly with respect to a floor surface in a state of being stored in the storage room.

9. A particle radiation therapy apparatus comprising:
a bed configured to perform positioning of a patient by moving in space of a treatment room;
an irradiation port configured to output a particle beam in the treatment room, the particle beam having been transported through a fixed beam transportation path;
a horizontal-direction imaging unit provided with a first X-ray source and a first X-ray detector that face each other along a horizontal line with the bed interposed between the first X-ray source and the first X-ray detector;
a vertical-direction imaging unit provided with a second X-ray source and a second X-ray detector that face each other along a vertical line with the bed interposed between the second X-ray source and the second X-ray detector;
a fourth support member that is
installed in the treatment room at a position other than a floor side,
configured to displace the first X-ray detector horizontally and then displace the first X-ray detector upward when the horizontal-direction imaging unit is not in use, and
further configured to position the first X-ray detector between the bed and a side of the irradiation port when the horizontal-direction imaging unit is in use.

\* \* \* \* \*